(12) United States Patent
Abraham et al.

(10) Patent No.: US 9,846,244 B2
(45) Date of Patent: Dec. 19, 2017

(54) PHOTON COUNT CORRECTION

(75) Inventors: Doug Abraham, Topsfield, MA (US); Basak Ulker Karbeyaz, Medford, MA (US); Olivier Tousignant, St-Lazare (CA)

(73) Assignee: ANALOGIC CORPORATION, Peabody, MA (US)

( * ) Notice: Subject to any disclaimer, the term of this patent is extended or adjusted under 35 U.S.C. 154(b) by 250 days.

(21) Appl. No.: 14/347,994

(22) PCT Filed: Sep. 30, 2011

(86) PCT No.: PCT/US2011/054203
§ 371 (c)(1),
(2), (4) Date: Mar. 27, 2014

(87) PCT Pub. No.: WO2013/048436
PCT Pub. Date: Apr. 4, 2013

(65) Prior Publication Data
US 2014/0326894 A1    Nov. 6, 2014

(51) Int. Cl.
*G01T 1/17*       (2006.01)
*G01N 23/04*      (2006.01)
(Continued)

(52) U.S. Cl.
CPC ............. *G01T 1/17* (2013.01); *G01N 23/046* (2013.01); *H04N 5/32* (2013.01); *H04N 5/3655* (2013.01)

(58) Field of Classification Search
CPC ....................................................... G01T 1/17
See application file for complete search history.

(56) References Cited

U.S. PATENT DOCUMENTS

| | | | | |
|---|---|---|---|---|
| 4,897,788 A | * | 1/1990 | King | A61B 6/583 |
| | | | | 378/12 |
| 5,818,052 A | * | 10/1998 | Elabd | H01L 27/14665 |
| | | | | 250/370.06 |

(Continued)

FOREIGN PATENT DOCUMENTS

| | | | | |
|---|---|---|---|---|
| CH | WO 2011015235 A1 | * | 2/2011 | ............... G01T 1/17 |
| JP | 62-191787 | | 8/1987 | |

(Continued)

OTHER PUBLICATIONS

Korean Office Action cited in Japanese Application No. 2014-533267 dated Aug. 4, 2015, 7 pgs.

(Continued)

*Primary Examiner* — David Porta
*Assistant Examiner* — Jeremy S Valentiner
(74) *Attorney, Agent, or Firm* — Cooper Legal Group, LLC

(57) ABSTRACT

One or more techniques and/or systems are described for addressing (e.g., during calibration) pixel-by-pixel variations in an image modality that utilizes photon counting techniques, such as by adjusting a number of photons detected by certain pixels (e.g., redistributing or reallocating detected photons among pixels). Such variations may cause an effective area of one or more pixels of a detector array to be larger than the effective area of other pixels, resulting in more photons being counted by some pixels than others, which can degrade resulting images. Accordingly, photons are redistributed as provided herein so that, when exposed to substantially uniform radiation, photon counts of neighboring pixels are substantially equal, statistical noise among neighboring pixels is substantially equal, and a signal-to-noise ratio among neighboring pixels is substantially equal. By redistributing photons as described herein, a spatial (Continued)

uniformity and/or a modulated transfer function (MTF) associated with a detector array may be improved.

20 Claims, 6 Drawing Sheets

(51) Int. Cl.
*H04N 5/32* (2006.01)
*H04N 5/365* (2011.01)

(56) References Cited

U.S. PATENT DOCUMENTS

| | | | |
|---|---|---|---|
| 6,748,043 B1* | 6/2004 | Dobbs | G01N 23/046 378/16 |
| 2007/0075888 A1* | 4/2007 | Kelly | H03M 1/145 341/155 |
| 2007/0098139 A1* | 5/2007 | Hoffman | A61B 6/4241 378/19 |
| 2009/0021607 A1* | 1/2009 | Takenaka | A61B 6/00 348/231.99 |
| 2010/0086102 A1* | 4/2010 | Kameshima | G01T 1/00 378/62 |
| 2011/0019034 A1* | 1/2011 | Chou | H04N 5/3655 348/241 |
| 2011/0101231 A1 | 5/2011 | Rundle | |
| 2011/0168909 A1* | 7/2011 | Nakao | G01T 1/247 250/370.09 |
| 2011/0210235 A1* | 9/2011 | Dierickx | G01T 1/17 250/214 R |
| 2012/0126131 A1* | 5/2012 | Ballabriga | G01T 1/17 250/370.08 |

FOREIGN PATENT DOCUMENTS

| | | |
|---|---|---|
| JP | 20044532998 A | 10/2004 |
| JP | 2007000632 A | 1/2007 |
| JP | 2009300295 A | 12/2009 |

OTHER PUBLICATIONS

International Search Report cited in related application No. PCT/US11/54203 dated Jun. 15, 2012, pp. 14.

Tlustos, et al., "Fixed pattern deviations in Si pixel detectors measured using the Medipixl readout chip", Nuclear Instruments & Methods in Physics Research. Section A: Accelerators, Spectrometers, Detectors, and Associated Equipment, Elsevier BV, North-Holland, Netherlands, vol. 509, No. 1-3, Aug. 21, 2003, pp. 102-108.

Communication pursuant to Article 94(3) EPC in related EP Application No. 11 767 882.1 dated Oct. 17, 2017 (8 pgs).

* cited by examiner

PHOTON COUNT CORRECTION

BACKGROUND

The present application relates to the field of image modalities. It finds particular application to image modalities that employ photon counting techniques (e.g., such as image modalities that employ x-ray and/or gamma radiation) and/or to spatial uniformity correction and/or to modulated transfer function (MTF) improvement (e.g., optimization) for image modalities that implement photon counting. For example, medical, security, and/or industrial applications may utilize a computed tomography (CT) scanner comprising photon counting pixels to count the number of photons that are detected by respective pixels and, based upon the number of photons detected by respective pixels, one or more images providing a two-dimensional and/or three-dimensional representation of an object under examination may be generated therefrom.

Today, CT and other image modalities (e.g., single-photon emission computed tomography (SPECT), mammography, digital radiography, etc.) are useful to provide information, or images, of interior aspects of an object under examination. Generally, the object is exposed to radiation comprising photons (e.g., such as x-rays, gamma rays, etc.), and an image(s) is formed based upon the radiation absorbed by the interior aspects of the object, or rather an amount of photons that is able to pass through the object. Generally speaking, highly dense aspects of the object (e.g., or aspects of the object having a composition comprised of higher atomic number elements) absorb more radiation than less dense aspects, and thus an aspect having a higher density, such as a bone or metal, for example, will be apparent when surrounded by less dense aspects, such as muscle or clothing.

Radiographic image modalities generally comprise, among other things, a detector array comprised of a plurality of pixels that are respectively configured to convert radiation that has traversed the object into signals that may be processed to produce the image(s). The pixels are typically one of "charge integrating" and "photon counting" type pixels (e.g., the image modality operates in charge integration mode, photon counting mode, or both).

Charge integrating type pixels (e.g., pixels comprising charge integrating channels) are configured to convert energy into signals (e.g., current or voltage signals) that are proportional to an incoming photon flux rate. Respective signals may then be integrated over a time period (e.g., referred to herein as a measurement interval), sampled, and digitized. While this type of pixel is widely used, there are several drawbacks to such pixels. For example, charge integrating type pixels are generally not able to provide feedback as to the number and/or energy of photons detected. Moreover, there is a lower limit of detection defined by noise in the pixel such that a pixel with little to no incident radiation may produce some signal due to thermal and/or analog read noise (e.g., produced by the detector array and/or readout components). It will be appreciated that as a result of this lower limit, the dose of radiation that is applied to an object under examination is generally greater than the dose of radiation that may be applied to the object if the pixels are of a photon counting type.

Photon counting type pixels (e.g., pixels comprising photon counting channels) are configured to convert energy into signals that are proportional to the energy of a detected photon (e.g., also referred to herein as a radiation event). Thus, ideally, signals produced by respective pixels generally comprise one or more current and/or voltage pulses, for example, respectively associated with a single radiation event. A controller may then be used to determine the location and energy of respective radiation events, accumulate the radiation events occurring during a measurement interval, digitize the information, and process the digital information to form an image, for example. It will be appreciated to those skilled in the art that there are numerous advantages to photon counting type pixels over charge integrating type pixels. For example, the counting of photons is essentially noise free (e.g., apart from inherent photon shot noise). Therefore, a lower dose of radiation may be applied to the object under examination. Moreover, photon counting type pixels generally allow for energy (e.g., or wavelength) discrimination. Therefore, images indicative of different energy levels of radiation may be obtained at the same time, for example.

While photon counting type pixels have numerous advantages over charge integrating type pixels, variations in the pixel area of respective photon counting type pixels (e.g., caused by manufacturing defects, electric field distortion, etc.) can be a significant source of spatial non-uniformity (e.g., causing intensity variations in resulting images). A pixel with a larger area tends to detect more photons to the detriment of one or more pixels adjacent to the pixel with the larger area. Conventionally, these variations in pixel area have been corrected by what is referred to in the art as a gain correction. As part of the gain correction, a calibration is performed and a multiplicative factor is found for respective pixels based on a ratio of the response of a pixel to which the multiplication factor is applied relative to an average response of neighboring pixels. For example, a pixel that counts fewer photons during the calibration (e.g., when a uniform dose is exposed to substantially all pixels of the detector array) than neighboring pixels may have a multiplicative factor of greater than one applied to it (e.g., such that the number of photons detected by the pixel during an examination is multiplied by the same multiplicative factor greater than 1).

As described above, the predominate (e.g., substantially only) source of noise in a photon counting detector array is expected to come from the statistical process of counting photons. The more photons detected by a pixel, the better the signal-to-noise ratio, which is equal to the square root of the number of photons counted by the pixel. By applying the multiplicative factor to the signal of a pixel, it will be appreciated that a similar multiplicative factor is also applied to the statistical noise of the pixel, causing the total noise of the pixel to increase or decrease (e.g., depending upon whether the multiplicative factor is greater than or less than 1) but the signal-to-noise ratio of the pixel to remain the same. Therefore, despite the gain correction, there may remain a variation in the signal-to-noise ratio of pixels neighboring one another, which may affect (e.g., reduce or degrade) resulting images.

SUMMARY

Aspects of the present application address the above matters, and others. According to one aspect a method is provided. The method comprises adjusting a number of photons detected by a first pixel of a detector array to yield an adjusted signal-to-noise ratio for the first pixel, the adjusted signal-to-noise ratio different than a first signal-to-noise ratio for the first pixel indicative of the number of photons detected by the first pixel.

According to another aspect a computer readable medium comprising computer readable instructions that when executed via one or more processors perform a method is provided. The method comprises that when a number of photons detected by a first pixel of a detector array deviates from an average number of photons detected by pixels adjacent to the first pixel by more than a specified threshold, the number of photons detected by the first pixel are adjusted such that when the first pixel and the pixels adjacent to the first pixel are exposed to substantially uniform radiation, a statistical noise associated with detecting photons by the first pixel is substantially equal to an average statistical noise associated with detecting photons by pixels adjacent to the first pixel.

According to yet another aspect a system for an image modality that employs photon counting technology is provided. The system comprises a correction component configured to adjust a number of photons detected by a first pixel of the image modality such that a signal-to-noise ratio is substantially uniform among the first pixel and pixels adjacent to the first pixel when the first pixel and the pixels adjacent to the first pixel are exposed to substantially uniform radiation.

According to another aspect a method for addressing pixel-to-pixel variations in an image modality that utilizes photon counting is provided. The method comprises exposing pixels of the image modality to a substantially uniform number of photons and determining an image gradient based upon a number of photons detected by respective pixels. The method also comprises determining a weighting function for respective pixels based upon the image gradient, the weighting function providing for a transfer of photons from a first pixel to a second pixel.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
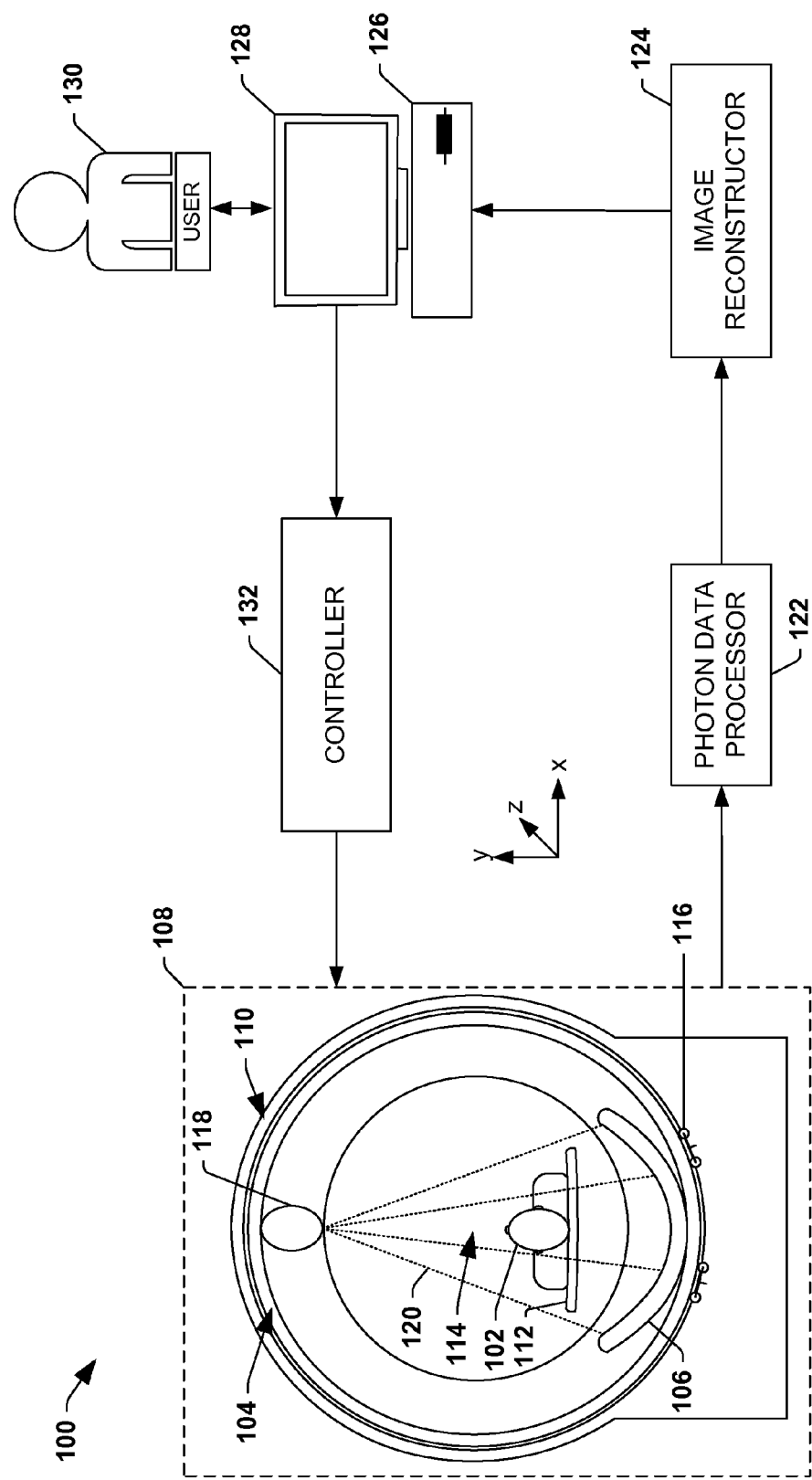
FIG. 1 is an example environment of a first image modality that employs photon counting technology.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques are provided herein for redistributing photons among neighboring pixels (e.g., correcting respective records of photon counts of respective pixels). Generally speaking, the redistribution results in the photon counts of neighboring pixels being substantially equally, the statistical noise of neighboring pixels being substantially equal, and the signal-to-noise ratio of neighboring pixels being substantially equal (e.g., within a specified deviation/tolerance of an average for the neighboring pixels) when a detector array is uniformly exposed to radiation, or rather exposed to substantially uniform radiation. In this way, pixel intensity spatial uniformity for image modalities which employ photon counting techniques and/or systems may be improved (e.g., optimized) and/or a modulated transfer function (MTF) may be improved (e.g., optimized), for example. Stated differently, the spatial resolution and/or the MTF (e.g., which is the spatial resolution of the detector array in a frequency domain), may be adjusted to improve the accuracy of the spatial resolution and/or MTF. For example, when one or more pixels count too many or too few photons, the accuracy of the spatial resolution and/or the MTF is reduced. By adjusting a record of the number of photons counted (e.g., detected) by one or more pixels, the spatial resolution and/or MTF may be restored (e.g., to what it would have been if respective pixels consumed or occupied the same surface area of the detector array).

The systems and/or techniques described herein generally provide for substantially uniformly exposing pixels of a detector array to photons during a calibration phase and recording an image. An image gradient may then be determined for the pixels and a weighting function for a pixel (e.g., primary pixel) that has a photon count that is outside of a specified threshold relative to the photon count of neighboring pixels may be determined. Based upon the determined weighting function, a photon transfer table (e.g., also referred to herein as a kernel) may be established that specifies how to adjust the photon count of a pixel during subsequent examinations (e.g., after calibration). Such a photon transfer table may be used to correct one or more images resulting from an examination of an object (e.g., occurring after calibration).

It will be appreciated that while continued reference is made herein to x-ray photons and examples are provided that include the emission and/or subsequent detection of x-rays, the disclosure, including the scope of the claims, is not intended to be limited as such to the extent practical. For example, the photons may be x-ray photons, gamma photons, and/or other types of photons that are commonly emitted from image modalities (e.g., such as traditional CT, single-photon emission computed tomography (SPECT), mammography, digital radiography, etc.). Moreover, while reference is made herein to adjusting a number of photons detected, those skilled in the art will appreciate that this refers to an adjustment of a count. For example, while 150 photons may have been counted by a single pixel, a record of the detected photons may be adjusted to reflect that merely 100 photons were counted by the pixel (e.g., despite that 150 were actually counted).

It will also be appreciated that the examples provided herein, including numbers mentioned herein, are merely intended to be viewed as examples, and are not intended to necessarily correlate to practical implementations. For example, the radiation dose that is applied to the detector array is generally large enough to perform requisite calibrations and/or imaging functions. Thus, for example, in a practical implementation respective pixels may count 100,000 or more photons as opposed to 50-150 numbers illustrated in the examples provided herein.

FIG. 1 is an illustration of an example environment 100 of an example image modality that may be configured to generate data (e.g., images) representative of an object or an aspect thereof under examination. It will be appreciated that the example configuration is merely intended to be representative of one type of image modality (e.g., a third-generation CT scanner) and is described herein merely to provide one example image modality. That is, the disclosure, including the scope of the claims, is not intended to be limited to a particular type(s) of image modality(ies) to the extent practical, but rather the systems and/or techniques described herein may be used in conjunction with a wide variety of photon emitting image modalities, such as, but not limited to, SPECT, mammography, and/or digital radiography, etc., for example.

In the example environment 100, an examination unit 108 of the image modality is configured to examine one or more objects 102. The examination unit 108 can comprise a rotating gantry 104 and a (stationary) support structure 110 (e.g., which may encase and/or surround as least a portion of the rotating gantry 104 (e.g., as illustrated herein with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more radiation sources 118 (e.g., an ionizing x-ray source) and a detector array 106 comprised of a plurality of pixels (e.g., also referred to as detectors) that is mounted on a substantially diametrically opposite side of the rotating gantry 104 relative to the radiation source(s) 118.

During an examination of the object(s) 102, the radiation source(s) 118 emits fan, cone, wedge, and/or other shaped radiation 120 configurations from a focal spot of the radiation source 118 (e.g., a point within the radiation source(s) 118 from which radiation 120 emanates) and into the examination region 114. It will be appreciated by those skilled in the art that such radiation 120 may be emitted substantially continuously and/or may be emitted intermittently (e.g., a short pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear or two-dimensional array of pixels disposed as a single row or multiple rows in the shape of a circular, cylindrical, or spherical arc, for example, typically having a center of curvature at the focal spot of the radiation source(s) 118, for example. As the rotating gantry 104 rotates, the detector array 106 is configured to directly convert (e.g., using amorphous selenium and/or other direct conversion materials) and/or indirectly convert (e.g., using Cesium Iodide (CsI) and/or other indirect conversion materials) detected radiation into analog signals.

The detector array 106 is generally operated in a photon counting mode (e.g., as opposed to an integration mode). That is, the pixels are of a photon counting type (e.g., such as of a variety known to those skilled in the art) and are configured convert energy (e.g., in the case of CT scanners, x-ray energy) into signals that are proportional to the energy of detected photons (e.g., where the detection of respective photons may be referred to herein as a radiation event). Thus, ideally, signals produced by respective pixels generally comprise one or more current and/or voltage pulses, for example, respectively associated with a single radiation event. It will be appreciated that while specific reference is made herein to photon counting type pixels, the detector array 106 may also comprise charge integrating pixels. For example, respective pixels may comprise one or more photon counting channels and one or more charge integrating channels.

Signals that are produced by the detector array 106 or rather by pixels comprised in the detector array 106 may be transmitted to a photon data processor 122 that is in operable communication with the detector array 106. The photon data processor 122 (e.g., which may be referred to as a controller) is configured to receive the signals and generate photon data indicative of, among other things, a location and detection time for respective photons detected by the detected array.

The detection times of respective photons may respectively correlate to a particular position of the radiation source(s) 118 at those detection times. It will be appreciated that in some instances (e.g., because of practical limitations of the photon data processor 122), the photon data processor 122 may bin data related to the photons into acquisition bins based upon their respective detection times. For example, the photon data processor 122 may be unable to correlate each detected photon with a position of the radiation source(s) 118 at the instance respective photons were emitted, so the photon data processor 122 may bin the photons that were detected in a particular interval together and determine an approximate position of the radiation source 118 during that interval of time. It will be understood to those skilled in the art that the number of acquisition bins should be relatively large (e.g., one thousand) to reduce tangential blurring (caused when respective bins represent photons emitted during a larger span along the trajectory or movement of the radiation source(s) 118).

It will be appreciated that the photon data may be indicative of other characteristics of the detected photons besides detection time and location. For example, the photon data may include information related to an energy of detected photons and/or a trajectory/angle of respective photons from the radiation source(s) 118 to the detector array 106 (e.g., which may be derived by the photon data processor 122 based upon the location of a detected photon, the time it was detected, and a position of the radiation source(s) 118 at the instant the photon was detected).

The example environment 100 also illustrates as image reconstructor 124 that is operably coupled to the photon data processor 122 and is configured to generate one or more images representative of the object 102 under examination using suitable analytical, iterative, and/or other reconstruction technique (e.g., tomosynthesis reconstruction, back-projection, etc.). Generally, respective images focus on a plane (e.g., or slice) of the object 102 under examination.

It will be appreciated that as part of the reconstruction process by the image reconstructor 124 and/or as part of the recordation process by the photon data processor 122, for example, a specified number of photons (e.g., based upon a calibration process that will be described later) may be transferred (e.g., reallocated) from a first pixel to one or more pixels neighboring (e.g., adjacent to) the first pixel to improve signal and statistical noise uniformity in images produced therefrom. That is, a record of the number of photons counted by a pixel may be adjusted by a specified amount (e.g., as determined based upon a calibration process), and a difference between the original number and the adjusted number may be distributed to one or more neighboring pixels (e.g. such that the records of the one or more neighboring pixels are also adjusted).

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the examination unit 108 (e.g., a speed of rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

It will be appreciated that the example component block diagram is merely intended to illustrate one embodiment of one type of image modality and is not intended to be interpreted in a limiting manner. For example, the functions of one or more components described herein may be separated into a plurality of components and/or the functions of two or more components described herein may be combined into merely a single component. Moreover, the image modality may comprise additional components to perform additional features. For example, in one embodiment, the image modality further comprises a pulse shaper configured to shape detector signals and/or image characteristics of signals yielded from the one or more pixels (e.g., by discarding undesirable portions of the signal).

Figure 2:
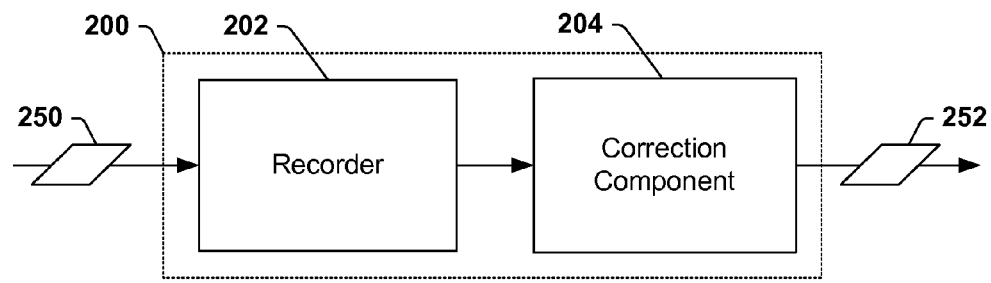
FIG. 2 is a component block diagram of an example photon data processor.

FIG. 2 illustrates a photon data processor 200 (e.g., 122 in FIG. 2) that is configured to receive signals 250 and generate photon data 252 indicative of, among other things, a location and detection time for respective photons detected by a detector array (e.g., 106 in FIG. 1). For example, the photon data processor 200 may receive signals 250 from the detector array and output photon data 252 to an image reconstructor (e.g., 124 in FIG. 1) for further processing and/or reconstruction (e.g., to yield images of an object under examination).

As illustrated, the example photon data processor 200 comprises a recorder 202 and a correction component 204. The recorder 202 is configured to record, among other things, a location and detection time for respective photons detected by respective pixels of the detector array. Moreover, it will be appreciated that the recorder 202 may, in one embodiment, record the number of photons respective pixels detected during a given period of time. That is, the recorder 202 (e.g., or another component of the photon data processor 200 not shown) may bin information about photons detected by respective pixels over a given time period. For example, the photon data processor 200 may record that in the first millisecond of the examination, a first pixel detected 100 photons, a second pixel detected 102 photons, etc., and in a next millisecond of the examination, the first pixel detected 98 photons, the second pixel detected 101 photons, etc. In this way, it can be determined how many photons respective pixels counted during a specified amount of time (e.g., which may be referred to herein as a measurement period and/or view).

It will be appreciated to those skilled in the art that while efforts are made during manufacturing to improve the precision of the pixels such that respective pixels of a detector array occupy or comprise a substantially same amount of area on a detector surface of the detector array, not every pixel may be identical. For example, manufacturing defects in one or more pixels may cause deviations in the area of one or more pixels. A pixel with a larger area generally detects more photons to the detriment of one or more pixels adjacent to the pixel with the larger area. That is, photons that would have been detected by a pixel adjacent the pixel with the larger area are instead detected by the pixel with the larger area causing spatial non-uniformities in an image(s) resulting therefrom (e.g., degrading image quality and/or image performance).

To address the differences in an effective area of respective pixels, the correction component 204 is configured to adjust the number of photons detected by one or more pixels based upon information provided in a photon transfer table (e.g., described below). For example, based upon a calibration, it may be determined that a first pixel typically counts or measures thirty percent more photons than pixels adjacent the first pixel. Therefore, the correction component 204 may transfer 30% of the photons counted by the first pixel (e.g., primary pixel) during a measurement period to one or more other pixels, adjacent to the first pixel (e.g., neighboring pixels), that typically count fewer photons than one or more other pixels adjacent the first pixel (e.g., which may count a number of photons within a specified threshold (e.g., deviation) of an average). It will be appreciated that while reference is made herein to transferring photons and/or adjusting a number of detected photons by a pixel based upon information provided in a photon transfer table, photons themselves are not actually transferred nor is the number of photons detected adjusted. Rather, what is meant by such language is that a record of the number of photons counted by a pixel is adjusted. For example, if a first pixel counts 150 photons and the information in the photon transfer table provides that 33% of those photons should be transferred to a second pixel that merely counts 50 photons, the correction component 204 may adjust a record of the first pixel to provide that 100 photons were counted by the first pixel and may adjust a record of the second pixel to provide that 100 photons were counted by the second pixel. In this way, the correction component 204 corrects for deficiencies caused by defects in the pixels (e.g., resulting in the first pixel having an area that is different (e.g., larger) than the second pixel).

It will be appreciated that, unless indicated to the contrary, terms such as "first," "second," and/or the like are merely used herein as identifiers, names, designations, etc. (e.g., to be able to distinguish different elements (e.g., pixels) from one another), and are not meant to imply an ordering, sequence, importance, temporal aspect, etc.

It will also be appreciated that adjusting a number of photons counted by respective pixels (e.g., by moving, shifting, reallocating, etc. photons counted by a first pixel to a record of a number of photons counted by a second pixel) is different than a gain correction that has traditionally been performed to compensate for the pixel to pixel variations. For example, during a gain correction, the number of photons (e.g., the signal) and the statistical noise resulting from the detected photons are multiplied by a multiplicative factor that is determined during a calibration. Such a multiplication results in the number of photons and the statistical noise changing, but the signal-to-noise ratio remaining constant.

As described herein, the correction is an adjustment to the number of photons counted by a pixel. That is, photons that are counted by a first pixel are transferred to one or more other pixels. Such an adjustment results in a number of photons detected changing, a statistical noise associated with the photons detected changing, and a signal-to-noise ratio associated with the first pixel changing. Moreover, as will be described in more detail below, the statistical noise and signal-to-noise ratio of the first pixel that result from the adjustment is substantially equal to (e.g., within an allowable deviation of) an average statistical noise and signal-to-noise ratio of adjacent pixels when the first pixel and the adjacent pixels are exposed to substantially uniform radiation (e.g., such as during a calibration procedure).

The photon transfer table that is used to determine how to adjust the number of photons detected by respective pixels may be derived from a calibration and may, in one embodiment, be dependent upon the energy level of radiation emitted by the radiation source. For example, a photon transfer table that is valid for x-rays emitted at 70 keV may not be valid for x-rays emitted at 90 keV. Therefore, a calibration may be performed for respective energy levels at which an image modality may operate and a plurality of photon transfer tables may be derived therefrom for use in correcting the records of pixels during an examination of an object.

Further, it will be appreciated that while the example component block diagram illustrates the correction has occurring within the photon data processor 200, such a correction component may be located elsewhere within an image modality. For example, in another embodiment, the correction may be performed as part of an image reconstruction process, and thus the correction component 204 may be part of an image reconstructor (e.g., 124 in FIG. 1). In yet another embodiment, the correction component 204 may be a separate component of the image modality (e.g., not comprised within a photon data processor and/or an image reconstructor).

Figure 3:
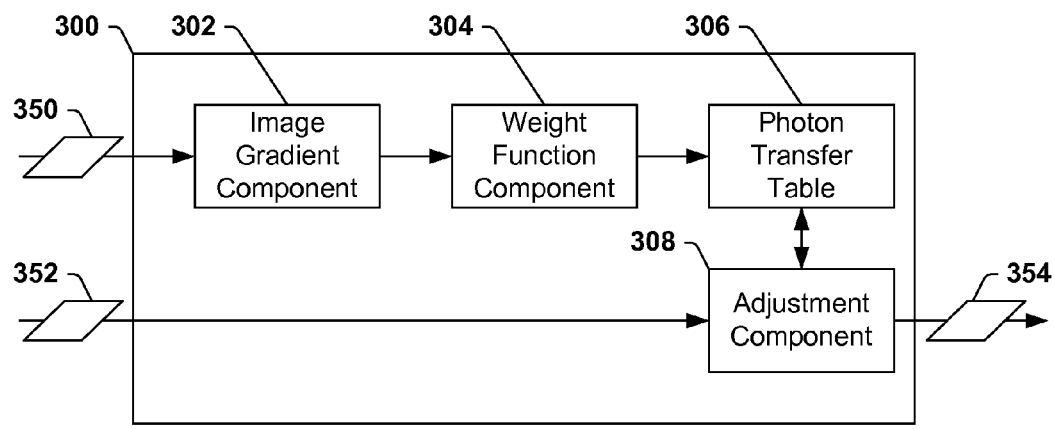
FIG. 3 is a component block diagram of an example correction component for adjusting a number of photons detected by one or more pixels.

FIG. 3 illustrates a component block diagram of an example correction component 300 (e.g., 204 in FIG. 2) that may be configured to adjust the number of photons one or more pixels detect (e.g., based upon a determination that a pixel detects too many to too few photons during a calibration procedure).

The correction component 300 comprises an image gradient component 302, a weight function component 304, a photon transfer table 306, and an adjustment component 308. It will be appreciated that at least some of these components may merely be utilized during a calibration procedure while other components may be utilized during both a calibration procedure and an examination of an object. For example, the image gradient component 302 and/or the weight function component 304 may be used merely during a calibration(s) while the photon transfer table 306 and/or the adjustment component 308 may be used during the calibration and during the examination (e.g., and imaging) of one or more objects.

During a calibration procedure, a radiation source (e.g., 118 in FIG. 1) substantially uniformly exposes a detector array (e.g., 106 in FIG. 1) to substantially uniform radiation (e.g., such that if respective pixels comprised the same area, substantially the same number of photons would be detected by respective pixels), and the correction component 300 receives calibration information 350 related to the number of photons detected by respective pixels during the calibration (e.g., from a recorder such as the recorder 202 in FIG. 2). That is, by exposing the pixels to a uniform amount of radiation, it can be determined which pixels have an area that exceeds a norm (e.g., an average area of pixels in a localized region of the detector array) and which pixels have an area that is below the norm based upon the number of photons detected by respective pixels. It will be appreciated that if the pixels comprised the same amount of detection surface, respective pixels should count a substantially similar number of photons because the detection surface of the detector array is being exposed to substantially uniform radiation.

An image gradient component 302 of the correction component 300 is configured to receive calibration information 350 related to the number of photons detected by respective pixels during the calibration procedure (e.g., when the pixels are substantially uniformly exposed to radiation). The image gradient component 302 may also be configured to identify a gradient (e.g., directional change in intensity of an image) or differences in the number of photons detected by respective pixels (e.g., such that a difference in the number of photons detected by a first pixel and the number of photons detected by one or more pixels adjacent the first pixel is determined). For example, in one embodiment, the image gradient component 302 is configured to determine an average number of photons detected by pixels adjacent a first pixel to determine whether the first pixel is within a specified threshold (e.g., deviation) from the average or is outside of the threshold. Such a process may be repeated for respective pixels until is it determined which pixels respectively counted a number of photons that is outside of the specified threshold and/or which pixels respectively counted a number of photons that is within of the specified threshold. It this way, it can be determined which pixels count too many photons and which pixels count too few photons relative to an average number of photons that are counted by the pixels of the detector array (e.g., or a localized region of pixels of the detector array), for example.

It will be appreciated that while reference is made herein to specific image gradient techniques that may be used by the image gradient component 302, the instant disclosure, including the scope of the claims is not intended to be limited as such to the extent practical. For example, other image processing techniques, such as those used to perform a flat-field correction, for example, may be used herein to identify differences in the photon counts for respective pixels.

The example correction component 300 also comprises a weight function component 304 that is used during a calibration procedure and is configured to determine how the number of photons detected by a pixel should be adjusted to bring the number within the specified threshold. That is the weight function component 304 is configured to determine whether photons, counted by a first pixel, should be transferred to one or more adjacent pixels that may have detected fewer photons than the average as a result of the first pixel detecting more photons than the average (e.g., because the area of the first pixel is larger than the average causing the area of the one or more adjacent pixels to be smaller than the average).

In one example, the weight function component 304 determines how the number of photons detected by a pixel should be adjusted by determining a percentage of the detected photons that should be transferred to another pixel based upon a difference between the number of photons counted by the first pixel and an average number of photons counted by pixels adjacent to the first pixel. For example, the image gradient component 302 may determine based upon the calibration that a first pixel counts 30% more photons than the average number of photons detected by other pixels (e.g., adjacent the first pixel), and the weight function component 304 may determine how the 30% of the photons detected by the first pixel should be transferred (e.g., distributed) to one or more pixels adjacent to the first pixel (e.g., based upon a determination by the image gradient component 302 that the one or more pixels adjacent the first pixel count fewer photons than the average number of photons). In this way, the weight function component 304 uses the information acquired during the calibration (e.g., when respective pixels should count a substantially equal number of photons) to determine how photons should be transferred from one pixel to another during an examination (e.g., when respective pixels may not count substantially equal number of photons due to an object attenuating a portion of the photons).

It will be appreciated that the weight function component 304 generally does not determine that photons should be merely discarded. Rather, the weight function component 304 is configured to determine how photons should be transferred from one pixel to one or more other pixels (e.g., adjacent the pixel that counted too many photons) such that the number of photons detected by adjacent pixels are substantially equal (e.g., within a specified tolerance) during the calibration. That is, the weight function component 304 is configured to determine how to reallocate detected photons amongst neighboring pixels in a manner that causes the pixels to respectively count a number of photons that is within a specified range of an average during the calibration. It will be appreciated that such a determination may be referred to as a weighting function, for example.

The weighting functions for respective pixels (e.g., the determination of what percentage of a photon count of a pixel should be transferred to one or more other pixels) are stored in a photon transfer table 306 of the example correction component 300. For example, referring to the example described with respect to the weight function component 304, the photon transfer table 306 may specify that during examinations, 30% of the photons counted by the first pixel may be deducted from the first pixel, with 80% of the deducted photons being transferred to a second pixel adjacent the first pixel and with the remaining 20% of those photons being transferred to a third pixel adjacent the first pixel (e.g., based upon a determination by the weighting function component 304 that the second and third pixels detected fewer photons than the average as a result of the first pixel detecting 30% more pixels than the average during the calibration).

The example correction component 300 also comprises an adjustment component 308 that is configured to adjust the records based at least in part upon information comprised in the photon transfer table 306. For example, during the calibration, the adjustment component 308 may adjust the calibration information 350 received from the recorder based upon the photon transfer table to output data 354 indicative of a corrected photon count (e.g., based upon the calibration) for respective pixels. In this way, it may be verified that the weight function component 304 determined how photons should be reallocated among pixels. For example, when the pixels are substantially uniformly exposed to radiation (e.g., such as during the calibration), data 354 that has been adjusted by the adjustment component 308 is generally indicative of a signal-to-noise ratio for respective pixels that is substantially uniform across the pixels. That is, after the adjustment component 308 adjusts, corrects, or updates the calibration information 350, a number of photons counted, a statistical noise, and a signal-to-noise ratio for respective pixels of a local region of pixels of the detector array should be substantially equal even though one of more pixels of the local region of pixels may have counted a substantially higher number of photons. Thus, if the resulting data 354 is indicative of such characteristics, the weight function component 304 correctly determined how photons should be transferred. If such characteristics are not substantially uniform, the calibration process may be repeated, for example.

The example correction component 300 is also configured to adjust information, or a record of the number of photons counted by one or more pixels during examinations based upon the photon transfer table. For example, the photon transfer table 306 may specify that when the radiation source is emitting radiation at 70 keV, 30% of the photons counted by a first pixel are to be transferred to a second pixel adjacent the first pixel. When the adjustment component 308 receives a record for the first pixel (e.g., included in examination information 352), the adjustment component 308 may transfer 30% of the photons counted by the first pixel to the second pixel as specified in the transfer table and may output the adjusted data 354 (e.g., to an image reconstructor). In this way, the adjustment component 308 causes the signal (e.g., number of photons counted), statistical noise associated with counting photons, and signal-to-noise ratio of one or more pixels that are part of the transfer to be adjusted. Moreover, it will be appreciated that if, during an examination and/or between examinations, the pixels (e.g., or a localized region of the pixels) are substantially uniformly exposed to radiation (e.g., to (re)test the appropriateness of adjustments being made), the resulting signals, statistical noise, and signal-to-noise ratio of the pixels exposed to the radiation should be uniform after an adjustment (e.g., reallocation) by the adjustment component 308.

Figure 4:
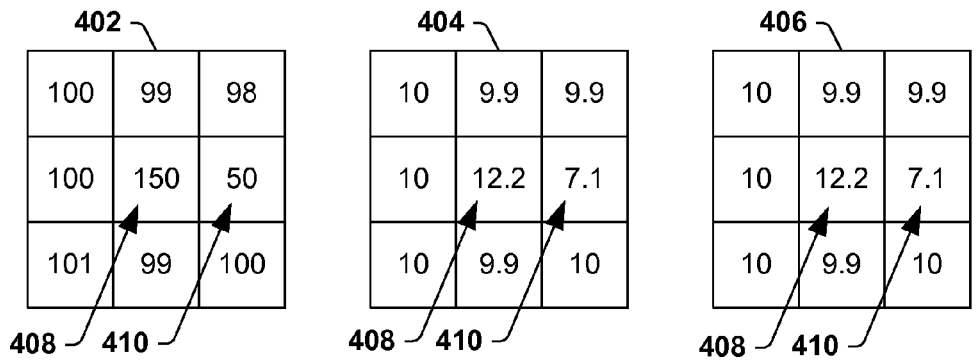
FIG. 4 is an example illustration of tables reflecting raw data for respective pixels.
Figure 5:
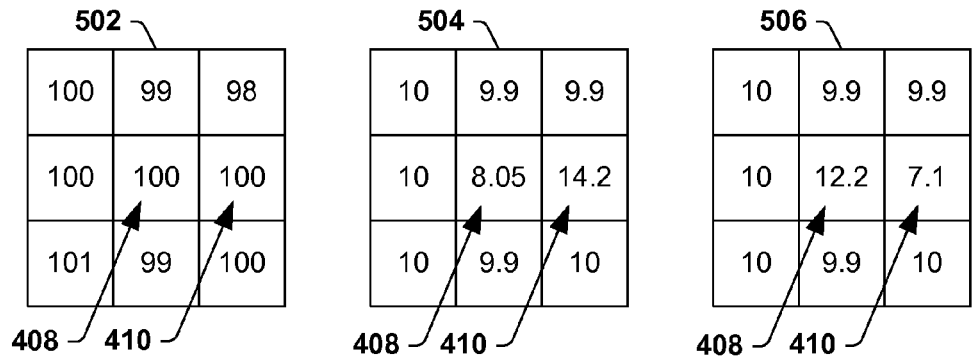
FIG. 5 is an example illustration of tables reflecting a number of photons counted, a statistical noise, and a signal-to-noise ratio after a gain-correction is applied to raw data.
Figure 6:
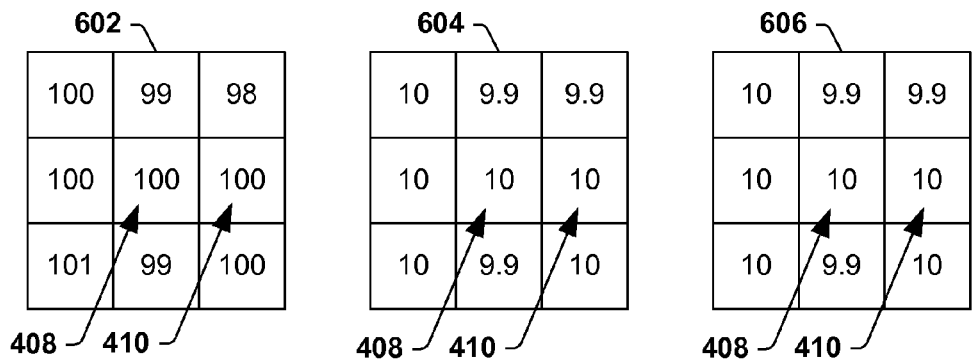
FIG. 6 is an example illustration of tables reflecting a number of photons counted, a statistical noise, and a signal-to-noise ratio after a correction technique as set forth herein is applied to raw data.

FIG. 4-6 illustrate tables providing information indicative of a signal (e.g., photon count), statistical noise associated with counting photons, and signal-to-noise ratio for respective pixels (e.g., of a localized region of nine pixels) of a detector array when radiation is substantially uniformly applied to the detector array (e.g., such as during a calibration). More particularly, FIG. 4 illustrates tables indicative of signals 402, associated statistical noise 404, and signal-to-noise ratios 406 for respective pixels of a detector array before a correction is applied. FIG. 5 illustrates tables indicative of signals 502, associated statistical noise 504, and signal-to-noise ratios 506 for respective pixels of a detector array after a conventional gain correction has been applied. FIG. 6 illustrates tables indicative of signals 602, associated statistical noise 604, and signal-to-noise ratios 606 for respective pixels of a detector array after an adjustment as set for herein has been applied.

As illustrated in FIG. 4, during a uniform exposure the table indicative of signals 402 yielded from respective pixels (e.g., where each square represents a pixel) provides that a majority of the pixels detected approximately 100 photons (e.g., within an allowable deviation of plus or minus two). However, as illustrated, a first pixel 408 detected 150 pixels (e.g., because of its larger area) to the detriment of a second pixel 410 that only detected 50 pixels. Because the statistical noise associated with detecting photons obeys a Poisson statistical process, the statistical noise associated with respective pixels is substantially equal to the square root of the photons detected by respective pixels as illustrated in the statistical noise table 404. Thus, in FIG. 4, the statistical noise associated with detecting pixels for a majority of the pixels is approximately 10 because the photons counted by the majority of the pixels is approximately 100. However, as a result of the increased photon count by the first pixel, the statistical noise associated with detecting photons by the first pixel 408 is greater than the average. Moreover, because the second pixel counted fewer photons than the average, the statistical noise associated with detecting photons by the second pixel 410 is less than the average. The same is true with the signal-to-noise ratios 406 of respective pixels, obtained by dividing the number of photons detected by respective pixels by the statistical noise for respective pixels, where the signal-to-noise ratios for respective pixels happens to be equal to the statistical noise for respective pixels in FIG. 4.

FIG. 5 illustrates tables indicative of signals 502, associated statistical noise 504, and signal-to-noise ratios 506 for respective pixels after a gain correction has been applied to compensate for pixel-by-pixel variations (e.g., which is a conventional technique). It will be appreciated that a gain correction generally operates by applying a multiplicative factor to the signal (e.g., photon count) yielded from pixels that are outside of a threshold. For example, as evident from the table 502, a multiplicative factor of 0.66 may be applied to the first pixel 408 to reduce the photon count from 150 to 100, and a multiplicative factor of 2 may be applied to the second pixel 410 to increase the photon count from 50 to 100 (e.g., to bring the photon count for the first and second pixels 408, 410 into alignment with the counts for other pixels).

As illustrated in the table 504 indicative of the statistical noise associated with detecting photons by respective pixels, by applying a multiplicative factor to the signal (e.g., photons), the multiplicative factor is also applied to the statistical noise. Therefore, the statistical noise associated with detecting pixels by the first pixel 408 is multiplied by a factor of 0.66 to yield a statistical noise of 8.05, and the statistical noise associated with detecting pixels by the second pixel 410 is multiplied by a factor of 2 to yield a statistical noise of 14.2. As illustrated in table 506 of the signal-to-noise ratios of respective pixels after a gain correction, the signal-to-noise ratio of respective pixels does not change from the signal-to-noise ratio illustrated in table 406 because both the signal and the statistical noise is multiplied by the same multiplication factor. Moreover, it will be appreciated that the corrected statistical noise as illustrated in table 504 and the signal-to-noise ratios for respective pixels as illustrated in table 506 are not uniform. That is, the first pixel 408, which counted more photons (e.g., as illustrated in table 402), has a signal-to-noise ratio and a statistical noise that is substantially different than the signal-to-noise ratio and statistical noise of pixels that counted a nearly average number of photons, for example.

FIG. 6 illustrates tables of the signals 602, statistical noise 604 associated with detecting photons, and signal-to-noise ratios 606 after a correction (e.g., or photon transfer) as described herein has been applied to pixels in need of such correction. For example, in table 602, it can be seen that 33% (e.g., 50) of the photons counted by the first pixel 408 were transferred to the second pixel 410 (e.g., so that both the first 408 and second 410 pixels have a count of 100 photons). In this way, the records of the first and second pixels 408, 410 are adjusted such that a photon count by respective pixels is within a specified threshold of other pixels adjacent the first and second pixels 408, 410, for example. Moreover, because photons were transferred, or rather a record was altered to reflect the transference of photons from the first pixel 408 to the second pixel 410, the statistical noise associated with detecting photons by the first and second pixels 408, 410 is merely the square root of the updated photon counts. Therefore, as illustrated in the statistical noise table 604, the statistical noise associated with detecting photons by the first pixel 408 and second pixel 410 are adjusted to values of 10 (e.g., the square root of 100). Moreover as illustrated in the statistical noise table 604, the statistical noise associated with detecting photons by respective pixels is substantially uniform (e.g., within a permissible threshold) upon the transference of photons using the systems and/or techniques herein described during a calibration.

It will be appreciated that the example tables of FIGS. 5-6 highlight some of the differences between correcting pixel-to-pixel area variations using a gain correction and the correcting such variations using techniques set forth herein. For example, comparing the statistical noise table 504 illustrated in FIG. 5 and the statistical noise table 604 illustrated in FIG. 6, it can be seen that whereas a correction using gain correction techniques results in a pixels having a non-uniform amount of statistical noise, the correction described herein results in both a uniform signal table 602 and a uniform statistical noise table 604 when radiation is uniformly applied to a group of pixels. Moreover, there are substantial differences in the signal-to-noise table 506 of FIG. 5 illustrating the signal-to-noise ratio of pixels upon a gain correction and the signal-to-noise table 606 of FIG. 6 illustrating the signal-to-noise ratio of pixels upon a correction as set forth herein. For example, whereas the gain correction technique results in signal-to-noise ratios for respective pixels that substantially match the initial signal-to-noise ratios of the pixels (e.g., before a correction is applied) as illustrated in the signal-to-noise ratio table 406 of FIG. 4, the correction techniques described herein result in signal-to-noise ratios for corrected pixels that are different than the initial signal-to-noise ratios of the corrected pixels. Further, it will be appreciated that when the pixels are substantially uniformly exposed to radiation (e.g., such as during a calibration), upon correction by the techniques herein described, the signal-to-noise ratio of respective pixels as illustrated in the corrected signal-to-noise ratio table 606 is substantially uniform (e.g., as opposed to the corrected signal-to-noise ratio table 506 of FIG. 5, where the signal-to-noise ratio of the first and second pixels 408, 410, are substantially different than the signal-to-noise ratio of other pixels represented in the table 506).

Figure 7:
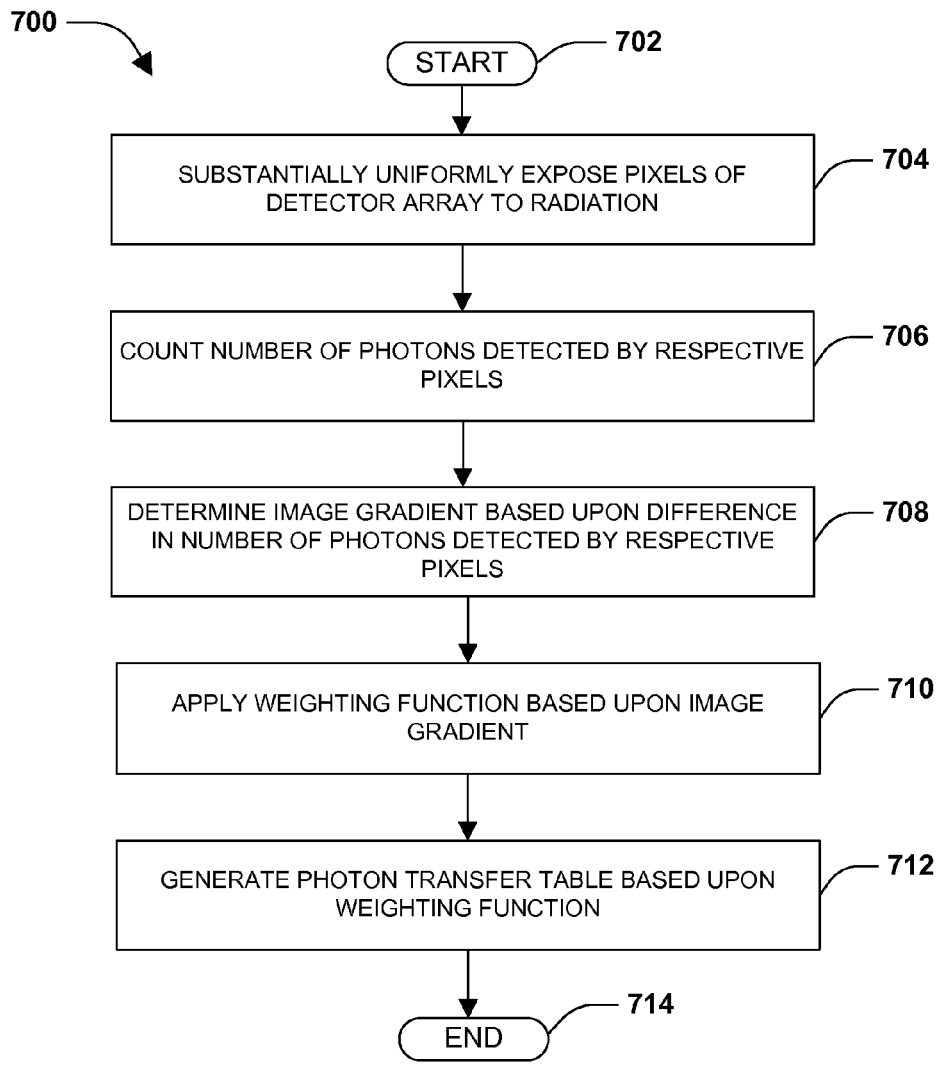
FIG. 7 is an example flow diagram illustrating an example method of calibrating an image modality to yield one or more photon transfer tables as set forth herein.

FIG. 7 illustrates an example method 700 for calibrating an image modality utilizing photon counting technology to improve spatial uniformity of images resulting from an examination of an object using the image modality. For example the example method 700 may identify the differences in photon counts amongst pixels and determine how to compensate for the differences by transferring a count of photons from a pixel that counted a higher than normal number of photons to one or more neighboring (e.g., adjacent) pixels. Such a method may replace and/or enhance a calibration process involved with utilizing a gain correction technique to compensate for pixel-to-pixel variations in the pixel area, for example, The example method 700 begins at 702 and pixels of a detector array are exposed to substantially uniform radiation at 704. It will be appreciated that the radiation may be x-rays, gamma-rays, and/or other forms of radiation that comprise photons and that may be used for imaging an object under examination. Moreover, while in a preferred embodiment an entire surface of a detector array is substantially uniformly exposed to radiation such that substantially all of the pixels of the detector array would detect a same number of pixels (e.g., if the surface area of respective pixels was the same), it will be appreciated that in another embodiments, merely a portion of the pixels may be substantially uniformly exposed to radiation at one time. For example, a first set of pixels may be exposed to radiation during a first interval of time and a second set of pixels may be exposed to radiation during a second interval of time. Thus, not all of the pixels of the detector array necessarily need to be exposed to radiation at the same time. Rather, merely the pixels that are to be calibrated may be substantially uniformly exposed to radiation.

At 706 in the example method 700, the number of photons detected by respective pixels is counted using analytical, iterative, and/or other photon counting techniques known to those skilled in the art. It will be appreciated that due to manufacturing defects or other defects in the pixels, some pixels may count more photons than other photons. For example, pixels that have a larger area due to manufacturing defects (e.g., manufacturing imprecisions), electric field distortions, etc., may detect more photons than adjacent pixels that have a smaller area. It will be appreciated that typically photons are not lost or gained. That is, pixels that detect more photons relative to nearby pixels generally do so to the detriment of one or more of the nearby (e.g., adjacent) pixels that detected too few photons. For example, if most pixels adjacent a first pixel detected 100 photons but the first pixel detected 150 photons, one or more pixels adjacent the first pixel probably detected fewer than 100 photons (e.g., because some of the photons that should have been detected/counted by the one or more adjacent pixels were instead detected/counted by the first pixel). Thus, as a result of pixel-to-pixel variations among the detection surface (e.g., area) of respective pixels, the photon counts of some pixels may be greater than the photons counts of other pixels (e.g., outside of a range that is considered tolerable).

As illustrated in FIG. 4 of the instant disclosure, the statistical noise associated with detecting photons by respective pixels and the signal-to-noise ratio of respective pixels is dependent upon the number of photons counted. For example, the statistical noise associated with counting photons is generally equal to the square root of the number of photons detected (e.g., obeying a Poisson statistical process), and electronic noise associated with electronic components of the pixels is typically negligible. Thus, the noise associated with counting photons by respective pixels is typically merely the square root of the number of photons detected by respective pixels. Moreover, the signal-to-noise ratio of a pixel can be derived from the number of photons detected because the noise is merely the square root of the number of photons detected by the pixel. Thus, the signal-to-noise ratio of a given pixel is the number of photons detected by the pixel (e.g., the signal) relative to the square root of the number of photons detected by the pixel (e.g., which in turn generally means that the signal-to-noise ratio of a pixel is merely the square root of the number of photons detected by that pixel).

At 708 in the example method 700 an image gradient is determined using analytical, iterative, and/or other image gradient techniques known to those skilled in the art. That is, differences between the number of photons counted by a first pixel during an interval of time (e.g., measurement period or view) and one of more pixels adjacent the first pixel are identified to determine whether the number of photons counted by the first pixel is outside of a norm (e.g., and thus should be corrected). For example, in one embodiment, the number of photons detected by pixels adjacent to and/or neighboring the first pixel are averaged to determine an average number of photons detected by pixels in a local region including (e.g., surrounding), the first pixel. The average number of photons detected by the pixels adjacent to and/or neighboring the first pixel is then compared to number of photons detected by the first pixel to determine whether the number of photons detected by the first pixel is within a specified tolerance (e.g., deviation) of the average. Such a process of determining an average and comparing the average to a pixel may be repeated for respective pixels of the detector array that are to be calibrated. Moreover, in one embodiment, as part of determining the image gradient at 708, pixels that fall outside of a specified range of the average may be marked or otherwise distinguished in a record (e.g., so that a photon count for those pixels can be adjusted).

At 710 in the example method 700, a weighting function is applied based upon the image gradient. Stated differently, when a pixel detects too many photons (e.g., relative to an average) during the calibration phase, it is determined by what percentage the number of photons should be decreased based upon the determined image gradient and transferred to one or more photons adjacent the pixel that detected too many photons. Conversely, when a pixel detects too few photons (e.g., relative to an average) during the calibration phase, it is determined what percentage of photons being transferred from another pixel should be received by the pixel that detected too few photons.

Stated differently, at 710 a decision is made on how to transfer photons based upon the nature of the pixel non-uniformity (e.g., whether a pixel detected too many or too few photons relative to neighboring pixels) that is caused by material defects, electric field distortion, etc. For example, if a first pixel detects approximately 150 photons and neighboring pixels detected around 100 photons, a decision may be made at 710 to transfer 33% of photons detected by the first pixel to one or more pixels adjacent the first pixel. Decisions may also be made to transfer 40% of the photons (e.g., 20 photons of the 50 being transferred) from the first pixel to a second pixel neighboring the first pixel if the second pixel detected around 80 photons during the uniform exposure, and to transfer 60% of the photons (e.g., 30 photons of the 50 being transferred) from the first pixel to a third pixel if the third pixel detected around 70 photons during the uniform exposure. Thus, the weighting function may determine the percentage of photons transferred from a pixel and a direction of the transference (e.g., which adjacent pixels are to receive what number/amount of photons being transferred).

It will be appreciated that while continued reference is made herein to transferring photons, photons themselves are generally not physically transferred. Rather, a record indicative of the number of photons counted by a particular pixel is adjusted to reflect a decisions specified by the weighting function(s). Thus, the weighting function describes how a record of the number of pixels detected by a pixel should be changed to account for pixel-to-pixel variations in the effective detection surfaces of respective pixels.

It will also be appreciated that finding an image gradient and/or applying a weight are merely tools for obtaining a photon transfer table and/or calibration matrix (e.g., providing information on how photons should be reallocated from one pixel to one or more neighboring pixels), and the instant disclosure, including the scope of the claims, is not intended to be limited as such to the extent practical. That is, one or more techniques other than (e.g., and/or in conjunction with) gradient and/or weighting may be implemented for identifying which pixels detected too many or too few photons and/or for determining how records of respective pixels should be updated, and such (other) techniques are contemplated herein.

At 712 in the example method 700, a photon transfer table (e.g., also referred to as a kernel) is generated based upon the weighting function(s). The photon transfer table generally provides information for respective pixels on how photons should be transferred from a pixel that detects too many photons (e.g., relative to an average number of photons detected by the pixels) to one or more pixels that detect too few photons. For example, the photon transfer table may specify that a pixel that counted too many photons during the calibration transfer 13.2% of photons counted by the pixel during examinations to a second pixel and 19.8% of photons counted by the pixel during examinations to a third pixel. In this way, records of pixels indicative of the number of photons counted may be updated in real-time as the photons are counted (e.g., and/or as data indicative of the number of photons counted by respective pixels is processed to produce images).

It will be appreciated that the photon transfer table may be merely valid for a particular level or range of radiation. Thus, where an image modality may function at a plurality of energy levels or ranges, the acts described above may be repeated for respective energy levels and/or ranges to generate photon transfer tables for respective energy ranges in which the image modality may operate, for example.

The example method 700 ends at 714.

Figure 8:
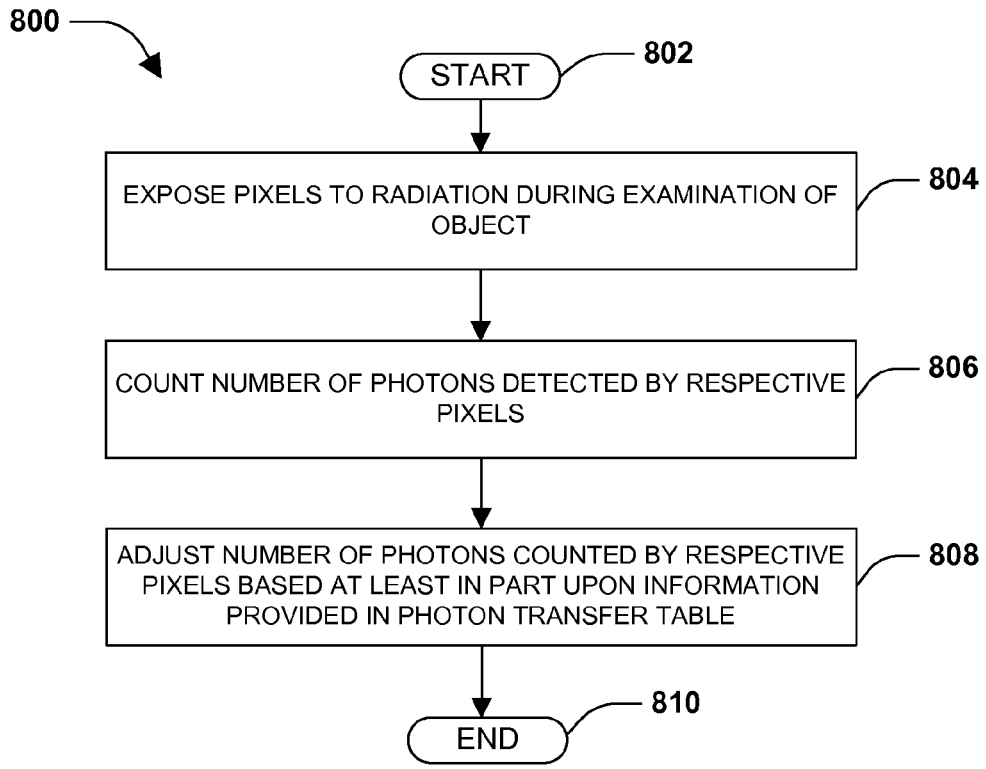
FIG. 8 is an example flow diagram illustrating an example method for adjusting a number of photons counted by one or more pixels using one or more photon transfer table as set forth herein.

FIG. 8 illustrates an example method 800 for correcting the number of photons counted by a pixel of a detector array of an image modality (e.g., such as a CT scanner, SPECT scanner, mammography, digital radiography, etc.). Using such a method 800, at least some adverse effects of pixel-to-pixel variations may be mitigated to improve spatial uniformity in images resulting therefrom and/or to improve signal and statistical noise uniformity in images resulting therefrom.

The example method 800 begins at 802, and pixels of a detector array of the image modality are exposed to radiation during an examination of an object at 804. That is, an object is inserted into an examination region of the image modality and radiation (e.g., comprising x-ray photons, gamma photons, etc.) is emitted towards the object in a fan, cone, wedge, or other shaped manner. Radiation that traverses the object is detected by pixels of the detector array on a diametrically opposite side of the examination region, for example, relative to a radiation source emitting the radiation.

At 806 in the example method, the number of photons detected by respective pixels is counted. That is, the pixels respectively generate a signal (current or voltage signal) indicative of a number of photons counted by respective pixels (e.g., which may be represented as pulses in the signal). Based upon the signals, a record indicative of, among other things, a number of photons detected by respective pixels may be generated. It will be appreciated that the record may also comprise other information that can be derived from the signal. For example, in one embodiment, an energy level of respective photons detected by a pixel is also recorded.

Because the object may attenuate varying amounts of energy, pixels may not detect a same number of photons. For example, fewer photons may traverse a bone than an organ and thus a pixel detecting photons that traverse the bone may count fewer photons than a pixel detecting photons that traverse the organ. It will be appreciated that unlike variations that occur when pixels are exposed to a substantially uniform amount of radiation (e.g., during calibration), variations in the number of photons detected (across different pixels) that occur when pixels are exposed to a non-uniform amount of radiation (e.g., such as when an object is being examined) is generally desired because such differences are used to generate an image(s) indicative of the object.

At 808, the number of photons counted by respective pixels, or a record of such a number, is adjusted based at least in part upon information provided in a photon transfer table (e.g., generated at 712 in the example method 700 of FIG. 7). That is, pixel-to-pixel variations caused by manufacturing defects, electric field distortions, etc., that were evident during a calibration (such as during the calibration described in the example method 700 of FIG. 7) are corrected (e.g., in real-time as part of an image creation process). For example, the photon transfer table may specify that a percentage (e.g., 33%) of pixels detected by a first pixel should be transferred to a second, adjacent pixel (e.g., based upon the calibration), and records of the number of photons counted by the first and second pixels respectively during the examination may be adjusted in accordance with what is specified in the photon transfer table. In this way, variations in the number of photons detected by respective pixels may be indicative of attenuation resulting from an examination of an object more so than variations resulting from manufacturing defects, electric field distortion, etc. (e.g., which may be evident when the pixels are uniformly exposed to radiation).

Moreover, it will be appreciated that as a result of the calibration (e.g., described with respect to the example method 700 of FIG. 7), when and/or if the pixels are uniformly exposed to radiation (e.g., such as between the examination of objects and/or during subsequent calibrations), numerous features may be evident in the signals and/or statistical noise attributes of respective pixels (e.g., relative to gain correction techniques that may be used to correct for pixel-to-pixel variations). For example, by adjusting a number of photons detected by a pixel, a signal-to-noise ratio for the pixel may be adjusted such that the adjusted signal-to-noise ratio is different than the signal-to-noise ratio that is indicative of the number of photons detected (e.g., as can be seen by comparing the signal-to-noise ratio table 406 of FIG. 4 to the signal-to-noise ratio table 606 of FIG. 6). Moreover, the signal-to-noise ratio of the pixel and the signal-to-noise ratio of other pixels respectively adjacent the pixel are substantially equal (e.g., within a specified deviation). Further, after adjusting the number of photons detected by respective pixels by transferring photons amongst pixels, the statistical noise associated with detecting photons by the respective pixels is substantially uniform across the pixels. Thus, after a calibration (where pixels are exposed to a substantially uniform amount of radiation), one or more adjustments may be made such that the signal, statistical noise, and signal-to-noise ratio are substantially uniform.

It will be appreciated that the example method 800 is merely intended to provide an example method for correcting for pixel-to-pixel variations caused by manufacturing defects, electric field distortions, etc. in image modalities that utilize photon counting and is not intended to fully describe a method for processing an image. That is, the example method 800 may be part of a method for processing an image, but is not intended to be inclusive of the all the acts that may be performed when processing an image. For example, additional calibrations and/or corrections may be applied to improve conversion efficiency (e.g., such as by taking pin-hole readings known to those skilled in the art) and/or acts may be provided for using the adjusted record of the number of photons counted by respective pixels to generate an image of an object (e.g., such as acts describing tomosynthesis reconstruction).

The example method ends at 810.

Figure 9:
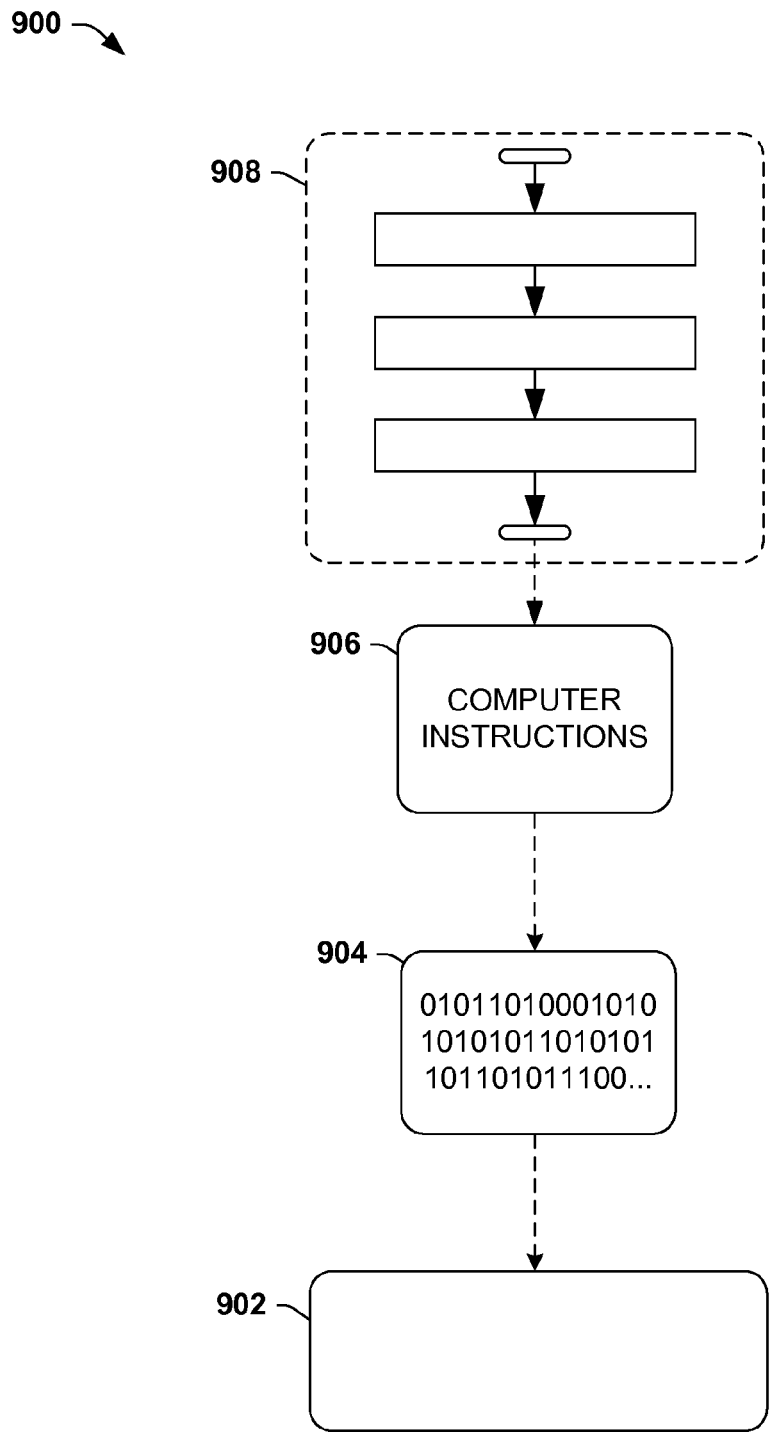
FIG. 9 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 9, wherein the implementation 900 comprises a computer-readable medium 902 (e.g., a flash drive, CD-R, DVD-R, or a platter of a hard disk drive), on which is encoded computer-readable data 904. This computer-readable data 904 in turn comprises a set of computer instructions 906 configured to operate according to one or more of the principles set forth herein. In one such embodiment 900, the processor-executable instructions 906 may be configured to perform a method 908, such as at least some of the example method 700 of FIG. 7 and/or at least some of the example method 800 of FIG. 8, for example. In another such embodiment, the processor-executable instructions 906 may be configured to implement a system, such as at least some of the exemplary systems 100, 200, and 300 of FIGS. 1, 2, and 3, respectively, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method comprising:
    recording a number of photons counted by a first pixel of a detector array to derive a first recorded count, wherein the first recorded count is associated with a first signal-to-noise ratio for the first pixel; and
    adjusting the first recorded count to yield a second recorded count for the first pixel, wherein the second recorded count is associated with a second signal-to-noise ratio for the first pixel, the second signal-to-noise ratio different than the first signal-to-noise ratio.

2. The method of claim 1, the adjusting comprising:
    subtracting, from the first recorded count, a specified percentage of the first recorded count.

3. The method of claim 2, comprising determining the specified percentage comprising:
    exposing the first pixel and one or more pixels adjacent to the first pixel to a substantially uniform amount of radiation;
    determining an average number of photons detected by the one or more pixels; and
    determining the specified percentage based upon a difference between the number of photons detected by the first pixel and the average number of photons detected by the one or more pixels.

4. The method of claim 1, comprising:
    adjusting a third recorded count indicative of a number of photons detected by a second pixel of the detector array adjacent to the first pixel based upon a difference between the first recorded count and the second recorded count.

5. The method of claim 1, wherein the first recorded count is associated with a first statistical noise and the second recorded count is associated with a second statistical noise different than the first statistical noise.

6. The method of claim 1, wherein the second signal-to-noise ratio for the first pixel is substantially equal to an average signal-to-noise ratio for one or more pixels of the detector array adjacent to the first pixel when the first pixel and the one or more pixels are exposed to substantially uniform radiation.

7. The method of claim 1, the photons comprising x-ray photons.

8. The method of claim 1, the photons comprising gamma photons.

9. A non-transitory computer readable medium comprising computer readable instructions that when executed perform a method, the method comprising:
   recording a number of photons counted by a first pixel of a detector array to derive a first recorded count for a measurement interval, wherein the first recorded count is associated with a first signal-to-noise ratio for the first pixel; and
   adjusting the first recorded count to yield a second recorded count for the first pixel for the measurement interval, wherein the second recorded count is associated with a second signal-to-noise ratio for the first pixel.

10. The non-transitory computer readable medium of claim 9, the method comprising determining an average number of photons detected by a group of pixels during a calibration phase.

11. The non-transitory computer readable medium of claim 10, the method comprising comparing the average number of photons detected by the group of pixels to a number of photons detected by the first pixel during the calibration phase.

12. The non-transitory computer readable medium of claim 9, the adjusting comprising subtracting, from the first recorded count, a specified percentage of the first recorded count.

13. The non-transitory computer readable medium of claim 12, the method comprising determining the specified percentage comprising:
   exposing the first pixel and a group of pixels to a substantially uniform amount of radiation;
   determining an average number of photons detected by the group of pixels; and
   determining the specified percentage based upon a difference between the number of photons detected by the first pixel and the average number of photons detected by the group of pixels.

14. The non-transitory computer readable medium of claim 9, the method comprising:
   adjusting a third recorded count indicative of a number of photons detected by a second pixel of the detector array adjacent to the first pixel based upon a difference between the first recorded count and the second recorded count.

15. The non-transitory computer readable medium of claim 9, wherein the second signal-to-noise ratio is substantially equal to an average signal-to-noise ratio for a group of pixels when the first pixel and the group of pixels are exposed to substantially uniform radiation.

16. The non-transitory computer readable medium of claim 9, comprising:
   adding at least a portion of a difference between the first recorded count and the second recorded count to a third recorded count for the measurement interval, the third recorded count indicative of a number of photons detected by a second pixel of the detector array adjacent to the first pixel.

17. The non-transitory computer readable medium of claim 9, the photons comprising x-ray photons.

18. The non-transitory computer readable medium of claim 9, the photons comprising gamma photons.

19. A method for addressing pixel-to-pixel variations in an image modality that utilizes photon counting, comprising:
   exposing pixels of the image modality to a substantially uniform number of photons;
   recording, during a calibration phase, photons detected by a first pixel to derive a first recorded count and photons detected by a second pixel neighboring the first pixel to derive a second recorded count;
   determining a weighting function based upon a difference between the first recorded count and the second recorded count, the weighting function specifying a percentage of photons counted by the first pixel that are to be subtracted from a count of photons detected by the first pixel and applied to a count of photons detected by the second pixel;
   recording the weighting function in a photon transfer table;
   recording, during a non-calibration phase, photons detected by the first pixel to derive a third recorded count and photons detected by the second pixel to derive a fourth recorded count; and
   retrieving the weighting function from the photon transfer table; and
   subtracting from the third recorded count a number of photons equal to the percentage as specified in the weighting function and adding the number of photons equal to the percentage to the fourth recorded count.

20. The method of claim 1, wherein at least one of:
   the second recorded count is greater than the first recorded count such that a number of photons attributed to being detected by the first pixel is greater than the number of photons detected by the first pixel, or
   the second recorded count is less than the first recorded count such that a number of photons attributed to being detected by the first pixel is less than the number of photons detected by the first pixel.

* * * * *